United States Patent [19]
Hatanaka et al.

[11] Patent Number: 6,133,343
[45] Date of Patent: Oct. 17, 2000

[54] RESINOUS COMPOSITION FOR DENTAL USE

[75] Inventors: Kenji Hatanaka; Satoshi Yamaguchi, both of Kurashiki; Mitsuo Otani, Nakajo-machi, all of Japan

[73] Assignee: Kuraray Co., Ltd., Kurashiki, Japan

[21] Appl. No.: 09/050,961

[22] Filed: Mar. 31, 1998

[30] Foreign Application Priority Data

Mar. 31, 1997 [JP] Japan .................................. 9-080904

[51] Int. Cl.[7] ...................................... C08L 51/00
[52] U.S. Cl. .......................... 523/201; 523/115; 523/116; 523/120; 524/533; 525/902
[58] Field of Search .................... 523/115, 120, 523/116, 201; 525/902; 524/533

[56] References Cited

U.S. PATENT DOCUMENTS

| | | | |
|---|---|---|---|
| 3,427,274 | 2/1969 | Cornell | 523/120 |
| 4,564,653 | 1/1986 | Kamata et al. | 525/902 |
| 5,182,332 | 1/1993 | Yamamoto et al. | 523/116 |
| 5,210,109 | 5/1993 | Tateosian et al. | 525/902 |

*Primary Examiner*—Andrew E. C. Merriam
*Attorney, Agent, or Firm*—Oblon, Spivak, McClelland, Maier & Neustadt, P.C.

[57] ABSTRACT

A cured product of a resinous composition for dental use is neither stained nor discolored while used in the mouth for long periods of time. In addition, the cured product of the composition is not discolored with hot water, and its impact strength is high. The composition is easy to handle, and its storage stability is good. The composition comprises (a) an impact-resistant resinous complex composed of a (meth) acrylic polymer and core-shell structured polymer particles having at least one hard polymer layer, at least one soft polymer layer and an outermost hard polymer layer, wherein the impact-resistant resinous complex contains ionic components in an amount not larger than 0.05% by weight of the resinous composition, (b) (meth)acrylate monomer, and (c) a polymerization initiator.

17 Claims, No Drawings

RESINOUS COMPOSITION FOR DENTAL USE

BACKGROUND OF THE INVENTION

1. Field of the Invention

The present invention relates to a resinous composition for dental use. More precisely, the invention relates to a resinous composition suitable for denture bases, denture rebases, orthodontical bases, denture repairs, mouth pieces and temporary crowns.

2. Description of the Background

In ordinary dental treatment in prosthodontics and orthodontics, resious compositions are used for prostheses for denture bases and orthodontical bases. For producing those prostheses, mainly employed is a method of mixing a powdery component consisting essentially of polymethyl methacrylate and a liquid component consisting essentially of methylmethacrylate, followed by polymerizing and curing the resulting mixture. However, this method has a problem in that the mixture must be kept as such for a while until it becomes plastic enough to be filled into a gypsum mold. In addition, since its viscosity increases with a lapse of time, the mixture, if left longer than a predetermined period of time, becomes too hard to use, and the application time of the mixture is limited anyhow. Further there is another problem in that the mixture involves bubbles during mixing the powdery component and the liquid component together and bubbles in the resultant cured product decrease the mechanical strength of the cured product and the impact resistance of the same.

To improve the impact resistance of the cured product, a resinous composition for dental use comprising a powdery elastomer was proposed (see Japanese Patent Laid Open (JP-A) No. Hei-1-275509). However, the proposed composition has poor dispersion of the powdery elastomer in it and therefore the impact resistance of the cured product is still not satisfactory. In addition, as the powdery elastomer is formed to be amorphous by grinding, the powdery elastomer is not satisfactorily miscible with resinous composition for dental use, and the mixing of the components is troublesome. Moreover, the elastomer, due to its component, often causes discoloration of the cured product while the product is set in the mouth for a long period of time, and the appearance of the cured product becomes aesthetically poor.

Also a composition for dental use comprising a rubber-graft copolymer, a (meth)acrylate monomer and a polymerization initiator was proposed (see JP-A Hei-3-63205). However, the proposed composition still has a problem in that since the rubber-graft polymer and the (meth)acrylate monomer are mixed by blending, the rubber-graft copolymer particles are aggregated in the composition and are poorly dispersed therein though the particles are miscible with (meth)acrylate monomer to some extent. Therefore, the impact resistance of the composition for dental use and for denture bases still is not satisfactory. In addition, the discoloration resistance of the cured product is not improved at all, and the appearance of the cured product is still aesthetically poor.

To improve the dispersibility of the rubber-graft copolymer in the composition, a different composition was proposed for denture bases comprising methyl methacrylate polymer particles containing an inner layer of a rubber-graft copolymer, a (meth)acrylate monomer and a polymerization initiator (see JP-A Hei-6-57157). Though the dispersibility of the above-mentioned polymer particles in the composition was improved, the proposed composition still has some problems in that the cured product of the composition is discolored with hot water and its mechanical strength decreases while it absorbs water because of a suspending and dispersing agent required in producing the polymer particles.

On the other hand, proposed was still another composition for denture bases comprising methyl methacrylate polymer particles coated with a rubber-graft copolymer, a (meth) acrylate monomer and an organic peroxide (see JP-A Hei-6-247824). The above-mentioned methyl methacrylate polymer particles show improved dispersibility in the composition. However, the composition still has problems in that the cured product of the composition is discolored with hot water to damage the aesthetic appearance of the denture bases and its mechanical strength decreases while it absorbs water, due to a coagulant used in producing the polymer particles.

As has been mentioned hereinabove, the conventional technique of improving the dispersibility of rubber-graft copolymer in resinous composition resulted in the improvement in the impact resistance of the cured product for dental use or denture bases. However, since the rubber-graft copolymer contains stabilizer or coagulant in large quantities that are used in producing the polymer, the resinous composition for dental use comprising the rubber-graft copolymer has problems in that its mechanical strength decreases while the cured product is used for a long period of time in the mouth and it absorbs water, and in that the cured product is discolored with edible dyes and hot water.

Further proposed was a polymerizable composition comprising polyfunctional crosslinking monomer or oligomer, crosslinked polymer and rubber-modified polymer (see JP-A Hei-7-286018), which has easy handling of the composition and provides cured products having improved impact resistance. However, it was realized that the above composition has a problem in that the impact resistance of the cured product is still unsatisfactory since it contains crosslinked polymer as the essential component for improving the handling of the composition. In addition, no improvement is attained in preventing the discoloration of the cured product of the composition.

SUMMARY OF THE INVENTION

The object of the present invention is to provide a resinous composition for dental use, which is free from the problems noted above, i.e. a resinous composition to produce the cured product having good impact resistance and no discoloration.

The present invention provides a resinous composition for dental use, comprising (a) an impact-resistant resinous complex which is composed of core-shell structured polymer particles having at least one hard polymer layer, at least one soft polymer layer and an outermost hard polymer layer thereon and (meth)acrylic polymer, and contains ionic components in total amount of not larger than 0.05% by weight, (b) (meth)acrylate monomer, and (c) a polymerization initiator.

The impact-resistant resinous complex used in the invention is either sea-island structured fine polymer particles comprising core-shell structured polymer particles and (meth)acrylic polymer, or particles conglomerates comprising core-shell structured polymer particles and (meth)acrylic polymer particles.

The composition comprising the sea-island structured fine particles or the particle conglomerates is superior to a mixture of core-shell structured polymer particles and (meth)acrylic polymer particles, and therefore the composition according to the present invention is kept as a more uniform mixture. This is believed to be one of the reasons responsible for the improvement in the impact resistance of the cured product formed from the composition.

DESCRIPTION OF THE PREFERRED EMBODIMENTS

The sea-island structured fine particles comprising core-shell structured polymer particles and (meth)acrylic polymer are produced by polymerizing core-shell structured polymer particles, (meth)acrylate monomer, and comonomer capable of copolymerizing with them. In these particles, the (meth) acrylic polymer is of the sea component, while the core-shell structured polymer particles are of the island component and dispersed in the sea component. A part of the core-shell structured polymer particles may be aggregated by themselves. The morphology of the sea-island structured fine particles is not specifically defined. Preferably, however, the sea-island structured fine particles have a mean particle size (i.e., diameter) of from 20 to 2000 $\mu$m in view of the good handleability of the particles in producing the composition.

The particle conglomerates comprising core-shell structured polymer particles and (meth)acrylic polymer particles are produced, for example, by a method of mixing a suspension of core-shell structured polymer particles and a suspension of (meth)acrylic polymer particles, or a method of adding under mixing (meth)acrylate polymer particles to a suspension of core-shell structured polymer particles. The particle conglomerates comprise a plurality of core-shell structured polymer particles and a plurality of (meth)acrylic polymer particles.

In the particle conglomerates, the core-shell structured polymer particles and (meth)acrylic polymer particles are aggregated at random or alternately; or (meth)acrylic polymer particles aggregate as a cover layer on the core-shell structured polymer particles; or the core-shell structured polymer particles aggregate as a cover on (meth)acrylic polymer particles.

The core-shell structured polymer particles have at least one hard polymer layer and at least one soft polymer layer, and have an outermost hard polymer layer. The terminology of hard polymer and soft polymer as referred to herein is based on the Tg of respective polymers being 30±10° C. in consideration of the use of the cured product in the mouth. Concretely, polymers having a Tg of not lower than 40° C. are hard polymers; while those having a Tg of lower than 20° C. are soft polymers. More preferably, polymers having a Tg of not lower than 50° C. are hard polymers, and those having a Tg of lower than 0° C. are soft polymers.

Of the hard polymer layer, the hard polymer per se has a Tg of not lower than 40° C., more preferably not lower than 50° C. Of the soft polymer layer, the soft polymer per se has a Tg of lower than 20° C., more preferably lower than 0° C. These polymers are prepared with at least one (meth) acrylate monomer of 40 to 100% by weight, another monomer copolymerizable with it of 0 to 60% by weight, and another polyfunctional monomer of 0 to 5% by weight so that their Tg may fall within the defined range.

The monomers constituting the hard polymer layer and the soft polymer layer of the core-shell structured polymer particles are mentioned below. The (meth)acrylates include methacrylates such as methyl methacrylate, ethyl methacrylate, butyl methacrylate, pentyl methacrylate, cyclohexyl methacrylate, and acrylates such as methyl acrylate, ethyl acrylate, butyl acrylate, 2-ethylhexyl acrylate, cyclohexyl acrylate, and benzyl acrylate. These (meth) acrylates may be used either singly or combined.

The other comonomers include dienic compounds such as 1,3-butadiene, 2,3-dimethylbutadiene, isoprene; aromatic vinyl compounds such as styrene, vinyltoluene, α-methylstyrene; N-substituted maleimides such as N-cyclohexylmaleimide, N-o-chlorophenylmaleimide, N-tert-butylmaleimide; and vinyl cyanide compounds such as acrylonitrile, methacrylonitrile. These may be used either singly or as combined.

The poly-functional monomers include allyl methacrylate, allyl acrylate, triallyl cyanurate, allyl cinnamate, allyl sorbate, diallyl maleate, diallyl phthalate, triallyl trimellitate, diallyl fumarate, ethylene glycol di(meth)acrylate, polyethylene glycol di(meth)acrylate, divinyl benzene, 1,3-butylene glycol di(meth)acrylate. These may be used either singly or as combined.

The outermost polymer layer of the core-shell structured polymer particles is preferably a hard polymer layer, so that the particles are well dispersible in (meth)acrylate monomers. The proportion of the outermost hard polymer layer in the resinous particle is not specifically defined, but is preferably from 10 to 80% by weight of the core-shell structured resinous particle.

The core-shell structured polymer particles may have any desired multi-layered structure. For example, the structure of the core-shell structured polymer particles may be any of a two-layered structure of soft polymer layer/hard polymer layer; a three-layered structure of hard polymer layer/soft polymer layer/hard polymer layer; a four-layered structure of soft polymer layer/hard polymer layer/soft polymer layer/ hard polymer layer; a four-layered structure of hard polymer layer/soft polymer layer/soft polymer layer/hard polymer layer, all as so disposed in that order from the side of the innermost layer.

Polymerization to give the core-shell structured polymer particles for use in the invention is not specifically defined, but preferred is conventional emulsion polymerization. The size of the core-shell structured polymer particles is not specifically limited, but may fall between 0.01 and 0.5 $\mu$m in diameter. For good impact resistance of the cured product, the particle size falls more preferably between 0.05 and 0.3 $\mu$m.

The (meth)acrylic polymer particles to be in the resinous complex of the invention are of a hard polymer comprising at least one (meth)acrylate unit of 50 to 100% by weight and other comonomer units of 0 to 50% by weight. Those (meth)acrylates and comonomer units may be selected from the monomers as mentioned hereinabove for the core-shell structured polymer particles so that the resulting (meth) acrylic polymers may have a Tg of not lower than 40° C., more preferably not lower than 50° C. The (meth)acrylic polymer particles preferably have a mean particle size (i.e., diameter) of from 20 to 2000 $\mu$m, so that their handling in producing the composition is good.

A resinous composition which comprises the impact-resistant resinous complex comprising the core-shell structured polymer particles noted above, (meth)acrylate monomer and polymerization initiator, gives a cured product for dental use with good impact resistance. However, it has heretofore been said that the composition still has problems that when the cured product of the composition is used for a long period of time in the mouth, the impact resistance of the cured product decreases and the cured product is discolored.

Taking the problems into consideration, the present inventors have unexpectedly found after their intensive study that the ion content of the impact-resistant resinous complex has a great influence on the durability of the cured product of the composition in the mouth. Specifically, when the total amount of ionic components of the impact-resistant resinous complex containing core-shell structured polymer particles is 0.05% by weight or more, the cured product of the composition is greatly colored with edible dyes, and becomes opaque when exposed to hot water to damage its appearance. The cured product, after having been once opaque, could not recover its original appearance, and greatly loses its transparency. In addition, its mechanical strength decreases when the cured product absorbs water. As a result, the cured product could not maintain its good impact resistance for a long period of time.

The ionic components include, for example, alkali metal ions such as sodium and potassium ions; and alkaline earth metal ions such as magnesium and aluminium ions.

The resinous complex as produced according to the methods mentioned above may be easily separated, for example, by adding coagulant to the suspension of the reaction product to thereby coagulate the product, or directly spraying and drying the suspension. Apart from those methods, the suspension may be freeze-coagulated to separate the resinous complex.

Studies have revealed that the resinous complex as manufactured by the coagulant addition and by spray-drying have a large total amount of ion components, while the resinous complex manufactured by the freeze-coagulation has a small amount of ion components.

To make the impact-resistant resinous complex containing core-shell structured polymer particles which have an ion content of not larger than 0.05% by weight, the complex has to be separated from the suspension thereof by freeze-coagulation. When freeze-coagulating the suspension containing the complex, the complex particles are coagulated by their physical coagulation without any ionic coagulant. In this process, the emulsifier used in polymerization moves into water and is removed from the complex. The freeze-coagulated particles of the complex are separated from the suspension, then melted, and dehydrated to obtain the resinous complex particles having total amount of ion components not larger than 0.05% by weight.

When the impact-resistant resinous complex is separated by adding coagulant to the suspension containing the resinous complex or by spray drying the suspension, and the resinous complex therefore has a large ion content, the resinous complex must be subjected to at least one or more treatments of rinsing with hot water, ion exchanging, and separation by acid additive, thereby removing the ionic components to control the total amount of ionic components of the treated resinous complex to be not larger than 0.05% by weight.

The coagulant employable in the process of separating the complex from the suspension includes, for example, sulfates such as magnesium sulfate and sodium sulfate, chlorides and acetates.

The component (b), (meth)acrylate monomer to be in the resinous composition for dental use of the invention may be any of mono-functional (meth)acrylates and polyfunctional (meth)acrylates.

The mono-functional (meth)acrylates include alkyl (meth)acrylates (in which the alkyl group has from 1 to 25 carbon atoms), and other (meth)acrylates. Examples are alkyl(meth)acrylates (in which the alkyl group has from 1 to 25 carbon atoms), such as methyl(meth)acrylate, ethyl (meth)acrylate, butyl(meth)acrylate, hexyl(meth)acrylate, decyl(meth)acrylate, lauryl(meth)acrylate, myristyl(meth) acrylate, stearyl (meth)acrylate; and methoxyethyl(meth) acrylate, 2-phenoxyethyl(meth)acrylate, methoxypolyethyleneglycol (meth)acrylate (having a degree of polymerization of from 2 to 10), tetrahydrofurfuryl(meth)acrylate, isobornyl (meth)acrylate, undecenyl(meth)acrylate, benzyl (meth) acrylate, 2-hydroxyethyl(meth)acrylate (HEMA), and dimethylaminoethyl(meth)acrylate.

The poly-functional (meth)acrylates include alkyleneglycoldi(meth)acrylates (in which the alkylene group has from 1 to 20 carbon atoms), such as ethylene glycoldi(meth)acrylate, propyleneglycoldi(meth)acrylate, 1,4-butanedioldi(meth)acrylate, neopentyleneglycol di(meth)acrylate, 1,6-hexanedioldi(meth)acrylate, 1,10-decanedioldi(meth)acrylate; polyalkyleneglycol di(meth) acrylates (in which the alkylene group has from 2 to 4 carbon atoms and which has a polymerization degree of from 2 to 200), such as diethyleneglycoldi(meth)acrylate, triethyleneglycoldi(meth)acrylate, dipropyleneglycol di(meth)acrylate, polyethyleneglycoldi(meth)acrylate; and glycerindi(meth)acrylate, 2,2'-bis[p-($\gamma$-methacryloxy-$\beta$-hydroxypropoxy)phenyl]propane (Bis-GMA), bisphenolA dimethacrylate, 2,2'-di(4-methacryloxypolyethoxyphenyl) propane (having from 2 to 10 ethoxy groups in one molecule), 1,2-bis(3-methacryloxy-2-hydroxypropoxy) butane, trimethylolpropanetri(meth)acrylate, pentaerythritol tetra(meth)acrylate, and urethane(meth)acrylate. One or more of these (meth)acrylate monomers may be used either singly or as combined.

The polymerization initiator may be any of photo-polymerization initiators, thermal polymerization initiators, and chemical polymerization initiators.

The photo-polymerization initiators include $\alpha$-diketones such as camphor-quinone, diacetyl, 2,3-pentanedione, benzil, acenaphthene-quinone, phenanthraquinone; acylphosphine oxides such as 2,4,6-trimethylbenzoyldiphenylphosphine oxide; and benzoin methyl ether, benzyldimethyl ketal, benzophenone, and 2-ethylthioxanthone.

These photo-polymerization initiators may be used with a reducing agent of, for example, tertiary amines, aldehydes and mercaptans forming a photo-polymerization initiator catalyst system.

The tertiary amines include N,N-dimethylaminoethyl methacrylate, ethyl N,N-dimethylaminobenzoate, bis-N,N-dimethylaminobenzophenone, N,N-dimethylaminobenzaldehyde, N-phenylglycine, morpholino methacrylate, triethanolamine, N-methyldiethanolamine, 2-n-butoxyethylN,N-dimethylaminobenzoate, and isoamyl N,N-dimethylaminobenzoate.

The aldehydes include citronellal, laurylaldehyde, o-phthaldialdehyde, and p-octyloxybenzaldehyde.

The mercaptans include 1-decanethiol, thiosalicylic acid, 2-mercaptobenzoxazole, 2-mercaptobenzothiazole, 2-mercaptobenzimidazole, 4-mercaptoacetophenone, and 4-t-butylthiophenol.

Also preferably used is a system comprising the photo-polymerization initiator and organic peroxide such as benzoyl peroxide.

The thermal polymerization initiators include peroxides such as benzoyl peroxide, di-t-butyl peroxide, cumene hydroperoxide; azo compounds such as azobis isobutyronitrile; and tetramethyl thiuram disulfide.

The cold polymerization initiators may be redox initiators of, for example, organic peroxide/aromatic tertiary amine, or organic peroxide/aromatic tertiary amine/aromatic sulfinic acid.

Where a combination of oxidizing agent and reducing agent is used as the polymerization initiator, the two must be separately packaged so that they are not mixed together during storage, and mixed just prior to use, in order to ensure the storage stability of the initiator system.

In the resinous composition for dental use of the invention, the amount of the impact-resistant resinous complex is from 5 to 80% based on the weight of the composition. If the resinous complex content was smaller than 5% by weight, the impact resistance of the cured product is poor. If it was larger than 80% by weight, the discoloration resistance of the cured product is poor. The amount of the (meth)acrylate monomer is from 10 to 80% by weight of the composition, and that of the polymerization initiator is from 0.05 to 5% by weight in the composition.

The resinous composition for dental use of the invention may optionally contain any organic fillers (e.g., polymethyl methacrylate), inorganic fillers (e.g., silica powder), organic composite fillers, fibrous reinforcing materials and the like, thereby further increasing the hardness and the abrasion resistance of the cured product. In addition, it may further contain any of polymerization inhibitors (e.g., hydroquinone, hydroquinone monomethyl ether, butylhydroxyltoluene), oxidation stabilizers, ultraviolet absorbents (e.g., benzophenone), pigments, dyes, and fibers for mimic blood vessels.

Now, the invention is described in more detail by following Examples. The tests in the Examples were carried out according to the methods mentioned below.

EXAMPLES (1) Impact Resistance Test for Cured Product:

The impact resistance of the cured product was evaluated in a fracture toughness test, which was carried out according to the method disclosed in the literature (Dental Materials and Appliances, by Matsumoto, Vol. 7, No. 5, pp. 756–768, 1988). A paste composition was filled into a square pillar mold having a size of 2.5×5×30 mm and having a notch of 2.5 mm in depth formed with a cutter at the center, covered with a glass plate, and heated in hot water at 100° C. for 1 hour to cure it. For the fracture toughness of the sample of the cured product, measured were both the initial value of the fracture toughness and the value of the fracture toughness of the sample after processed in hot water.

The initial value of the sample was measured after it was dipped in water at 37° C. for 1 day, and a second value was measured after it was processed in hot water, i.e. the sample was first dipped in water at 37° C. for 1 day and then in water at 100° C. for 1 hour. Using an Instron universal tester (manufactured by Instron Co.), each sample was tested to measure its fracture toughness, at room temperature, at a cross-head speed of 1 mm/min, and at a fulcrum-to-fulcrum distance of 20 mm, whereupon the point at which the sample was broken was recorded to be the fracture toughness strength of the sample.

(2) Staining Test with Edible Dye:

The stain resistance of cured products was evaluated according to the method disclosed in the literature (Journal of Prosthetics, by Takamata Vol. 35, No. 3, pp. 542–555, 1991). A paste composition was filled into a disc mold having a thickness of 1 mm and a diameter of 2 cm, and heated in hot water at 100° C. for 1 hour to cure it. To determine its stain resistance, the sample of the cured product was dipped in an aqueous solution of 2% by weight of coffee (product of NESTLÉ Co.) at 37° C. for 7 days, and the change in its color before and after the coffee dipping was measured with a color-difference meter (manufactured by Nippon Denshoku KK).

(3) Discoloration Test in Hot Water:

Samples were prepared in the same manner as in the staining test. Each sample was dipped in hot water at 100° C. for 1 hour, and the change in its transparency before and after the dipping was measured with a color-difference meter (manufactured by Nippon Denshoku Kogyo Co., Ltd.), from which was evaluated the opaque resistance of the sample.

Example 1

In the following Examples ER-450 refers to three-layer core-shell structured particles in which the central layer is a copolymer of methylmethacrylate, ethylacrylate and allylmethacrylate; the second layer is a copolymer of butylacrylates, styrene and allylmethacrylate; and the outermost layer is a copolymer of methylmethacrylate and ethylacrylate.

M203 refers to sheath-core particles in which the core layer is a copolymer of butylacrylate and a comonomer, and the sheath layer is a copolymer of methylmethacrylate and a comonomer.

In Comparative Example 5, ACRON No. 5 consists of two packages, the powder is PMMA and BPO; the liquid is MMA monomer.

A composition was prepared which was comprised of particle conglomerates EB-S of 65 g (manufactured by Kuraray Co.; this is a freeze-coagulated product having a total content of ion components of 0.0277% by weight), i.e. particle conglomerates of core-shell structured polymer particles ER-450 (manufactured by Kuraray Co.) and (meth) acrylic polymer particles, methyl methacrylate of 35 g (manufactured by Wako Pure Chemical Industries, Ltd.; this is hereinafter referred to as MMA), and benzoyl peroxide of 1.0 g (manufactured by NOF Corp.; this is hereinafter referred to as BPO). The fracture toughness, the stain resistance and the discoloration resistance of the cured product of the composition were measured, and the results are shown in Table 1. In Table 1, also shown are the results of the cured products prepared and tested in the following Examples and Comparative Examples.

Example 2

A composition was prepared which contained 65 g of particle conglomerates (spray dried and rinsed with hot water, total content of ion components is 0.0488% by weight) composed of ER-450 and (meth)acrylic polymer particles, 35 g of MMA, and 1.0 g of BPO.

Example 3

A composition was prepared which contained 65 g of a resinous complex A, i.e. sea-island structured fine particles composed of ER-450 and (meth)acrylic polymer (separated by salting-out and followed by rinsing with hot water, and having total content of ion components of 0.0453% by weight: the production method for this is set forth in Reference Example 1), 35 g of MMA, and 1.0 g of BPO.

Example 4

A composition was prepared which contained 45 g of EB-S, 15 g of MB30X-20, i.e. cross-linked polymethacrylate polymer powder (manufactured by Sekisui Plastics Co.,), 40 g of MMA, and 1.0 g of BPO. The crosslinked polymethacrylate powder makes the composition pasty since the powder does not dissolve but swells in the composition.

Example 5

A composition was prepared which contained 50 g of EB-S, 5 g of 100B, i.e. polymethylmethacrylate powder (manufactured by Sekisui Plastics Co., Ltd.), 45 g of triethyleneglycoldimethacrylate (manufactured by Shin-Nakamura Chemical Co.), and 1.0 g of BPO. With a combination of triethyleneglycoldimethacrylate, EB-S and polymethylmethacrylate powder, wherein the monomer swells the two polymers but does not dissolve them, the resultant composition has stable viscosity and is pasty.

Example 6

A composition was prepared which was comprised of 55 g of EB-S, 5 g of Aerosil 380 (manufactured by Nippon Aerosil Co., ltd.) of silica powder, 40 g of MMA, and 1.0 g of BPO.

Comparative Example 1

A composition was prepared which contained 65 g of particle conglomerates composed of ER-450 and (meth)acrylic polymer particles (separated by salting-out, and having total content of ion components of 0.0711% by weight), 35 g of MMA, and 1.0 g of BPO.

Comparative Example 2

A composition was prepared which contained 65 g of particles conglomerates composed of ER-450 and (meth)acrylic polymer particles (prepared by spray-drying, and having total content of ion components of 0.223% by weight), 35 g of MMA, and 1.0 g of BPO.

Comparative Example 3

A composition was prepared which contained 35 g of resinous complex A, 35 g of MMA, and 1.0 g of BPO.

Comparative Example 4

A composition was prepared which contained 65 g of M203 (commercially manufactured by Kanegafuchi Chemical Co., and having a total content of ion components of 0.0800% by weight) of core-shell structured polymer particles, core-shell structured polymer particles, 35 g of MMA, and 1.0 g of BPO.

Comparative Example 5

A commercially available denture bases, ACRON No. 5 (manufactured by G-C Corporation) was mixed in a ratio of 70 g of its powder to 30 g of its liquid, and kept at room temperature for 25 minutes, and the resulting dough was filled into a mold, and cured in water at 100° C. for 1 hour.

Reference Example 1

Production of Resinous Complex A:

To 1000 g of latex of ER-450 of core-shell structured polymer particles (this has a solid polymer content of 1 kg, and a slurry concentration of 28%), added was 1300 g of MMA containing 100 g of BPO therein. To this mixture, further added were 10 kg of deionized water, and 1000 g of an aqueous solution of 5% magnesium carbonate as the suspension dispersant. The resulting dispersion was heated at 80° C. for 8 hours to polymerize MMA. Subsequently 16 g of magnesium sulfate was added thereto, and further stirred at 60° C. for 1 hour. The particles were taken out of this liquid through filtration, and dried at 60° C. for 24 hours to obtain white particles of the resinous complex A. The thus-obtained particles were sea-island structured fine particles composed of ER-450 of core-shell structured polymer particles as dispersed in the matrix (sea) of PMMA.

TABLE 1

| | Amount of Ionic Component (wt. %) | Fracture Toughness (MPa · m½) initial value → after hot water treatment | Staining with Coffee ($\Delta E^*$) | Opaque by Hot Water $\Delta(\Delta L^*)$ |
|---|---|---|---|---|
| Example 1 | 0.0277 | 2.15 → 2.11 | 3.4 | 14.7 |
| Example 2 | 0.0488 | 2.11 → 2.03 | 4.3 | 16.7 |
| Example 3 | 0.0453 | 2.08 → 2.0 | 3.9 | 15.2 |
| Example 4 | 0.0277 | 2.07 → 2.03 | 3.9 | 14.5 |
| Example 5 | 0.0277 | 1.91 → 1.90 | 2.9 | 13.2 |
| Example 6 | 0.0277 | 1.90 → 1.92 | 3.1 | 13.1 |
| Comparative Example 1 | 0.0711 | 2.09 → 1.88 | 10.7 | 28.0 |
| Comparative Example 2 | 0.2230 | 2.08 → 1.66 | 25.6 | 63.1 |
| Comparative Example 3 | 0.0824 | 2.10 → 1.72 | 13.7 | 32.8 |
| Comparative Example 4 | 0.0800 | 1.57 → 1.34 | 30.9 | 25.1 |
| Comparative Example 5 | — | 1.61 | 3.3 | 12.1 |

As has been mentioned hereinabove, the resinous composition for dental use according to the present invention comprises impact-resistant resinous complex composed of core-shell structured polymer particles and (meth)acrylic polymer and contains ionic components in total amount of not larger than 0.05% by weight and (meth)acrylate monomer, provides the cured product to be used in the mouth for a long period of time without decrease of its mechanical strength due to its water absorption, discoloration with edible dyes and opaque by hot water.

This application is based upon Japanese patent Application No. 9–80904 filed with the Japanese Patent Office on Mar. 31, 1997, the entire contents of which are herein incorporated by reference.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A composition comprising an impact-resistant resinous complex, a (meth)acrylate monomer, a polymerization initiator, and less than 0.05%, based on the weight of the resinous complex, of an ionic component,
    wherein the resinous complex comprises a (meth)acrylate polymer and core-shell structured polymer particles,
    the core-shell structured polymer particles are comprised of at least three layers, consisting of a hard polymer layer, at least one soft polymer layer, and an outermost hard polymer layer.

2. A composition comprising an impact-resistant resinous complex, a (meth)acrylate monomer, a polymerization initiator, and less than 0.05%, based on the weight of the resinous complex, of an ionic component,
    wherein the resinous complex comprises a (meth)acrylate polymer and core-shell structured particles,
    the core-shell structured polymer particles are comprised of at least three layers, consisting of a hard polymer layer, at least one soft polymer layer, and an outermost hard polymer layer, and
    wherein said core-shell structured polymer particles have a mean particle diameter of from 0.01 to 0.5 µm.

3. The resin composition of claim 2, wherein said core-shell structured polymer particles have a mean particle diameter of from 0.05 to 0.3 µm.

4. The resinous composition of claim 1, wherein said resinous complex is comprised of a sea-island structured particles; and wherein said core-shell structured polymer particles are dispersed into the matrix of said (meth)acrylate polymer.

5. The resinous composition of claim 4, wherein the sea-island structured particles have a mean particle diameter of from 20 to 2,000 µm.

6. The resinous composition of claim 2, wherein said resinous complex is comprised of conglomerate particles; and said conglomerate particles are comprised of a plurality of said core-shell structured polymer particles and a plurality of particles of said (meth)acrylate polymer.

7. The resinous composition of claim 1, wherein the weight of said (meth)acrylate monomer is from 10% to 80% of the weight of the resinous composition.

8. The resinous composition of claim 1, wherein the weight of said resinous complex is from 5% to 80% of the weight of the resinous composition.

9. The resinous composition of claim 1, wherein said hard polymer layer of said core-shell structured polymer particles has a Tg of at least 40° C.

10. The resinous composition of claim 1, wherein said hard polymer layer of said core-shell structured polymer particles has a Tg of at least 50° C.

11. The resinous composition of claim 1, wherein said soft polymer layer of said core-shell structured polymer has a Tg below 20° C.

12. The resinous composition of claim 1, wherein said soft polymer layer of said core-shell structured polymer has a Tg below 0° C.

13. The resinous composition of claim 1, wherein the polymerization initiator is selected from the group consisting of a photo-polymerization initiator, a thermal polymerization initiator and a chemical polymerization initiator.

14. The resinous composition of claim 1, further comprising a component for increasing hardness and abrasion resistance selected from the group consisting of an organic filler, an inorganic filler, an organic composite filler and a fibrous reinforcing material.

15. The resinous composition of claim 1, wherein said impact-resistant resinous complex is prepared by freeze-coagulating a resinous complex suspension containing sea-island structured particles or conglomerate particles, in the absence of a coagulant and separating the coagulated resinous complex, so that it contains ionic components in a total amount of less than 0.05% by weight.

16. The resinous composition of claim 1, wherein said impact-resistant resinous complex is prepared by adding a coagulant to a resinous complex suspension containing sea-island structured particles or conglomerate particles and separating the coagulated resinous complex and thereafter subjecting the separated resinous complex to a treatment selected from the group consisting of rinsing with hot water, ion exchange and separating by an acid additive, thereby reducing the content of ionic components to an amount of less than 0.05% by weight.

17. The resinous composition of claim 1, wherein said impact-resistant resinous complex is prepared by spray-drying a resinous complex suspension containing sea-island structured particles or conglomerate particles and thereafter subjecting the spay-dried resinous complex to a treatment selected from the group consisting of rinsing with hot water, ion exchange and separating by an acid additive, thereby reducing the content of ionic components to an amount of less than 0.05% by weight.

* * * * *